United States Patent [19]

Nichols

[11] Patent Number: 5,019,087
[45] Date of Patent: May 28, 1991

[54] NERVE REGENERATION CONDUIT

[75] Inventor: Joseph Nichols, Princeton, N.J.

[73] Assignee: American Biomaterials Corporation, Plainsboro, N.J.

[21] Appl. No.: 915,512

[22] Filed: Oct. 6, 1986

[51] Int. Cl.[5] .......................... A61F 2/06; A61B 17/04
[52] U.S. Cl. ........................................ 606/152; 623/1; 623/13
[58] Field of Search ............... 128/334 R, 334 C, 335, 128/335.5, DIG. 8, 92 YQ, 92 YR; 435/1, 240, 284; 530/356; 514/8, 21; 106/161; 623/1, 13; 606/152

[56] References Cited

U.S. PATENT DOCUMENTS

| 3,551,560 | 12/1970 | Thiele | 128/334 R |
|---|---|---|---|
| 3,833,002 | 9/1974 | Palma | 128/334 R |
| 4,325,867 | 4/1982 | Eberle et al. | 530/356 |
| 4,376,071 | 3/1983 | Jennings et al. | 435/240 |
| 4,448,718 | 5/1984 | Yannas et al. | 530/356 |
| 4,451,397 | 5/1984 | Huc et al. | 128/DIG. 8 |
| 4,544,552 | 10/1985 | Fraefel et al. | 435/240 |
| 4,621,631 | 11/1986 | Paques et al. | 128/334 R |
| 4,642,120 | 2/1987 | Nevo et al. | 128/92 YR |
| 4,642,293 | 2/1987 | Chung | 435/172.2 |
| 4,662,884 | 5/1987 | Stensaas | 128/335.5 |

OTHER PUBLICATIONS

Summary of Heyl (European) Patent; doc. #0,52,288; 623/13; May, 1982.
Rosen et al., "Suture and Sutureless Methods of Repairing Experimental Nerve Injuries", Chap. 25 of *Nerve Repair & Regeneration*, Jewett et al. eds., 1979.
Abstract of Madison et al., "Increased Rate of Peripheral Nerve Regeneration Using Bioabsorbable Nerve Guides and a Laminin Containing Gel", J. of Experimental Neurology, Jun., 1985, vol. 88(3), pp. 767–772.
Madison et al., "Nontoxic Nerve Guide Tubes Support Neovascular Growth in Transected Rat Optic Nerve", Experimental Neurology 86, pp. 448–461, (1984).
*In re Boe and Duke,* 184 VSPQ 38, (CCPA 1974).

*Primary Examiner*—Randall L. Green
*Assistant Examiner*—Paul Prebilic

[57] ABSTRACT

The present invention is directed to a hollow conduit comprised of a matrix of Type I collagen and laminin-containing material which conduit is used to promote nerve regeneration across a gap of a severed nerve. Methods of making the nerve regeneration conduit are also disclosed.

10 Claims, No Drawings

NERVE REGENERATION CONDUIT

BACKGROUND OF THE INVENTION

1. Field of the Invention

This invention pertains to the field of mammalian nerve regeneration. More specifially, the present invention relates to a conduit comprised of a matrix of Type I collagen and laminin-containing material which conduit is used to promote nerve regeneration of a severed nerve so as to bridge a gap between the severed ends of said nerve. Methods of making the nerve regeneration conduit are also disclosed.

2. Discussion of Related Art

Since the first reported attempt at surgical nerve repair in the thirteenth century, the restoration of normal nerve function following nerve injury has remained a persistently elusive goal. It was believed that damage to nerves resulted in a permanent loss of all function due to the failure of the nerve tissue to regenerate. It was then learned that the regenerative capacities of both the peripheral nervous system and the central nervous system are considerable, if the appropriate conditions are provided. The search for the best "appropriate conditions" is ever ongoing since the basic mechanism of the factors controlling nerve regeneration still remain a mystery.

Many different approaches have been taken in an attempt to regenerate a nerve that has been subjected to trauma—be it a severed nerve or a nerve having a gap between its proximal and distal ends. One such technique involves the actual suturing of the proximal and distal ends of the severed nerve.

In spite of the evolution of the surgical microscope and a prodigious effort into refining techniques for accurate nerve approximation, the clinical results of surgical nerve repair are still disappointing. Scar tissue resulting from the surgical manipulations required for direct proximal-to-distal nerve suture frequently interferes with the growth of proximal stump axons into the distal nerve stump. If a substantial number of axons are prevented from crossing the anastomotic site, neuroma (painful nerve cell tumor) formation often results. As a result, prospects for achieving significant reennervation are reduced. The end result is a lack of full return of motor and/or sensory function. Additionally, the regenerative potential of the damaged proximal nerve is frequently unpredictable and poorly understood.

Severe nerve injuries have required microsurgical grafting to span a defect. This technique involves surgically grafting a piece of a nerve from another part of the body. This approach too has limitations. The area from which the nerve was removed is left without sensation. Moreover, the amount of nerve tissue that can reasonably be removed for such grafts is also limited. However, suture techniques and/or grafting have not always been sufficient for repair of a severe defect. Still further, suture under tension, gap reduction by stretching, mobilization, flexion of a joint, or rerouting may compromise sensitive intraneuronal vascularity, and autografts induce a second surgical site with requisite risks and complications. Moreover, in many instances, there was either no nerve growth or only growth of connective tissue. Thus, the functional results of surgical repair of peripheral nerve injuries have been disappointing in spite of improved surgical techniques.

Strategies have been devised for allegedly enhancing the regeneration of peripheral nerves (those outside the spinal cord and brain). Thus, protection of the site of a neurorrhaphy from infiltration with fibrous tissue and prevention of neuromatous formation by the use of wrappers, cuffs, or tubes of various materials have been practiced since 1880. At that time, it was attempted to interpose a drain of decalcified bone between the severed ends of a sciatic nerve. Fibrous union without return of function, however, generally resulted. In addition to decalcified bone and vessels, fascia lata, fat, muscle, parchment, Cargile membrane, gelatin, agar, rubber, fibrin film, and various metals have been used with varying degrees of success. Many materials failed because they incited a foreign body reaction, produced constricting scar tissue, were technically difficult to apply, or required secondary operation for their removal.

Various enhancements in both entubulation and nerve wrapping have continued in order to facilitate nerve repair. Both biodegradable and non-resorbable materials have been used to act as a channel to promote growth and regeneration in severed nerves which have been sutured together or in connection with nerve grafts.

More particularly, in "The Use of a Resorbable Wrapper for Peripheral-Nerve Repair" by David G. Kline, et al., (*Journal of Neurosurgery*, Vol. XXI, No. 9, pp. 737-750, 1964), for example, collagen is used as a wrapping material around a severed nerve which had been sutured to insulate the site from surrounding connective tissue and to promote longitudinal orientation of the connective-tissue elements of the nerve to allegedly reduce axonal disorganization and restrict the tendency for regenerating axons to escape into extraneural tissue.

The use of a non-resorbable tube to aid in the alignment and joining of severed nerves is disclosed in U.S. Pat. No. 3,786,817. Here, the ends of a severed nerve are inserted into the ends of a tube until the nerve ends are close to each other or touch each other at the center of the tube. A fluid such as nitrogen is passed though the tube to aid in regeneration.

In U.S. Pat. No. 4,534,349, an absorbable hollow tubular device is provided which allegedly enables the sutureless repair of lacerated, severed, or grafted nerves wherein the device is comprised of a body-absorbable polymer.

In an article entitled "Fascicular Tubulization: A Cellular Approach to Peripheral Nerve Repair" by Joseph M. Rosen, et al., (*Annals of Plastic Surgery*, Vol. 11, No. 5, November, 1983), a cellular approach to nerve repair is discussed in which a polyglycolic acid tube is used around the fascicle as an artificial perineurium to separate fibrous healing from axonal regeneration until the perineurium reestablished its continuity across the repair site. The polyglycolic acid tube was resorbed without major cellular injury to the nerve. It was found that the longitudinal orientation of the repairs by fascicular tubulization was more organized than repairs simply made by suture but that the number of axon counts remained the same.

It has also been realized that the distal and proximal ends of a severed nerve need not be brought into abutting relationship with one another in order to have nerve regeneration. Instead of using a nerve graft, attempts have been made at bridging a gap within a nerve by inducing its growth over a considerable distance using various entubulation materials and techniques.

Both bioresorbable and non-resorbable materials have been used in tubes for bridging nerve gaps. For example, resorbable hollow polyester and polyester-composite channels for bridging gaps of between 5 to 9 mm in a mouse sciatic nerve within 6 to 12 weeks are disclosed in "Synthetic Bioresorbable Polymers: Polyester and Polyester-Composite Guidance Channels for Peripheral Nerve Repair" by E. Nyilas, et al., (Trans. Soc. Biomater., 6, 85, 1983).

In "Nerve Repair Using a Polyglactin Tube and Nerve Graft: An Experimental Study in the Rabbit" by Hakan Molander, et al. (Biomaterials, Vol. 4, pp. 276-280, October, 1983), a sectioned tibial nerve was bridged using a polyglactin mesh-tube and compared with a conventional nerve grafting in a rabbit. Only minor differences were observed in the results obtained between the two different techniques. The use of resorbable collagen tubes to bridge nerve gaps is discussed in "Nerve Regeneration Through Collagen Tubes" by W. Colin, et al., (Journal of Dental Research July, 1984, pp. 987-993).

Various anatomical parts have also been used as an aid to bridging nerve gaps. Thus, a comparison was made between nerves which were anastomosed by a conventional epineural suturing technique and nerves which were allowed to grow together without tension within a venous sleeve to which they were attached by traction and antirotation sutures, in an article entitled "Utilization of Venous Sleeves in Peripheral Nerve Repair" by N. Calteux, et al., (Ann. Chir. Main, 3 (2), 149-155, 1984). Neuroma formation was found to be reduced in the sheathed nerves as compared to the sutured nerves. Additionally, nerve conduction after 3 months was found to be somewhat greater in the sleeved anastomosis group.

So too, empty perineurial tubes have also been used as channels for bridging nerve gaps as disclosed in "Fascicular Nerve Graft Using An Empty Perineurial Tube: An Experimental Study in the Rabbit" by Y. Restrepo, et al., (Microsurgery 4: 105-112, 1983) and in "Empty Perineurial Tube Graft Used to Repair A Digital Nerve: A First Case Report" by Y. Restrepo, et al., (Microsurgery 6: 73-77, 1985).

More recently, in an effort to even further improve upon nerve regeneration, particularly across a gap, various regeneration promotion agents have been added to the interior of tubes in the form of a filling. Thus, rat sciatic nerve regeneration across a gap has been accomplished using a silicone tube packed with a protein, collagen, and a glycosaminoglycan polysaccharide, chondroitin-6-sulfate, wherein these materials were cross-linked to form a porous network that is degradable by enzymes at rates that can be controlled during preparation, although the silicone tube itself is not biodegradable.

The use of a nerve guide made from polymers of synthetic poly D,L-lactates with 2% triethyl citrate as a plasticizer containing a collagen matrix containing fibrinogen and fibronectin is disclosed in "Non-toxic Nerve Guide Tubes Support Neovascular Growth in Transected Rat Optic Nerve" by R. Madison, et al., (Experimental Neurology, 86(3): 448-461, 1984). The addition of the collagen matrix containing fibrinogen and fibronectin to the lumens of the nerve guide tube is said to have increased the amount of neovascular growth through the nerve guide lumens in the optic nerve.

By using a bioresorbable nerve guide filled with a laminin-containing gel, it was reported by Madison, et al. in "Increased Rate of Peripheral Nerve Regeneration Using Bioresorbable Nerve Guides and a Laminin-Containing Gel", (Experimental Neurology, 88: 767-772, 1985) that in vivo axonal regeneration in mice was hastened.

Although improved results in nerve regeneration have been obtained through the use of tubes filled with nerve regenerating promoters, there is still much room for further improvement. Particularly, the manufacture of tubes filled with such promoting agents is a relatively expensive and tedious process. Moreover, it would still be desirable to provide a means by which an even greater number of myelinated axons are regenerated, a faster rate of nerve growth is achieved, and longer nerve gaps are spanned. A need still exists to fulfill such a need and still reduce or eliminate problems that have been encountered with prior art nerve repair attempts such as revascularization, excessive fibrosis, reorientation of nerve fibres, and the final poor return of function of the end organs.

SUMMARY OF THE INVENTION

Applicant has discovered a new conduit for nerve regeneration which eliminates or substantially reduces many of the disadvantages and problems associated with the prior art attempts at nerve regeneration.

More particularly, Applicant has discovered a nerve regeneration conduit which promotes nerve regeneration to an even greater extent than the tubes filled with various nerve regeneration promotion agents discussed above. Most importantly, these conduits are hollow and do not employ a promoter filling in the center thereof, thereby facilitating the ease of their manufacture. Instead, all of the nerve regenerating constituents are present as part of the walls of the conduit of the present invention.

Specifically, Applicant's hollow conduit for promoting the in vivo regeneration of a severed mammalian nerve so as to bridge a gap between its severed ends has walls comprised of a matrix of Type I collagen and laminin-containing material.

This novel hollow conduit is made by forming a dispersion containing Type I collagen and a laminin-containing material; adding a precipitating agent to the dispersion; and contacting the precipitate with a spinning mandrel to form a tubular collagen membrane.

Applicant's discovery embodies at least two distinct advantages over the prior art. Firstly, it eliminates the need for the use of a filling material so as to substantially uncomplicate the manufacturing process of the nerve regeneration tubes. Moreover, quite surprisingly and totally unexpectedly, Applicant has discovered that by placing a nerve regeneration promoter, specifically a laminin-containing material, within the walls of the conduit rather than as a filling within the center thereof (as has been done in the prior art), both the qualitative and quantitative characteristics of the resulting nerve regeneration substantially exceed that obtained with the prior art filled nerve regenerating tubes.

Thus, by using the conduits of the present invention in a manner such that the respective ends of a severed nerve are brought into contact with each end of the hollow conduit whose walls are comprised of a matrix of Type I collagen and laminin-containing material, greater numbers of regenerating axons are stimulated (many of which become myelinated), a substantial increase in the initial rate of the outgrowth of fibers and mylenated axons is produced, and the regenerating axons are able to span even longer gaps than previously associated with prior art entubulation devices. Without wishing to be bound by theory, it is believed that these unexpected and surprising results may be due, in part, by the absence of a filling in the center of the tube which may tend to impede the growth of the nerve fibers and axons through the center thereof.

By virtue of the present invention, longitudinal alignment of nerve tissue is provided, extraneural fibrous invasion is eliminated, and extrafascicular sprouting of axons is eliminated. Additionally, a regenerated nerve is consistently obtained growing in a central location down the lumen of the nerve conduit and innervating the distal nerve stump. Blood vessels are reformed and a tremendous amount of growth occurs. In addition, a large number of Schwann cells—nonneuronal cellular elements that provide structural support and insulation to nerve endings—are observed. The conduits of the present invention allow the Schwann cells to travel farther along the gap than they would in a tube filled with a gel promoter. The regenerated nerve tissue looks healthy, is highly vascularized and about 20 percent of the axonal fibers are surrounded by a fatty myelin sheath produced by Schwann cells that have migrated into the tube.

This regenerative growth is obtained with a conduit that has sufficient strength and processability at first but is biodegradable within 1 to 3 months. It permits nerve regeneration free from interference by scar tissue and produces a negligible inflammatory response in the surrounding tissue.

Accordingly, not only do the conduits of the present invention represent a significant improvement as to the economics and efficiency in preparing a nerve regeneration tube but, additionally, it represents the totally unexpected improvement that substantially better results are obtained than that associated with prior art entubulation devices, particularly in the rate of mylenated axon growth.

DETAILED DESCRIPTION OF THE INVENTION

One of the primary constitutents of the conduits of the present invention is Type I collagen. Collagen is a fibrous protein and constitutes the major protein component of skin, bone, tendon, ligament, cartilage, basement membrane and other forms of connective tissue. It is the most abundant protein in the animal kingdom. In bone, for example, collagen fibers reinforce the calcium phosphate mineral base. Despite its great strength, bone retains flexibility because of its collagen content.

Collagen has been used extensively in medicine and in surgery. Collagen based devices have been used, as noted above, as nerve regeneration tubes, as sutures, hemostatic fiber and sponges, wound dressings, neurosurgical sponges, injectable implants for soft tissue augmentation, pharmaceutical carriers, ophthalmic aqueous-venous shunts, contact lenses and the like.

The properties of collagen which favor its use as a biomaterial are many. It has a high order of tensile strength and low extensibility. Collagen is biodegradable, and when implanted in the body, is absorbed at a rate that can be controlled by the degree of intra or intermolecular cross-linking imparted to the collagen molecule by chemical or physical treatment. Collagen products can thus be designed such that, on implantation, they will be completely absorbed in a few days or in months. The collagen can also be chemically treated so that it becomes non-absorbable while still retaining its hydrophilic character and its good tissue response. Although native collagen is a very weak antigen, it can be made, for all practical purposes, immunologically inert by means well known to those skilled in the art.

The collagen molecule is a triple helix and has a unique protein conformation that is a coiled coil of three polypeptide subunits or alpha chains. Each alpha chain twists in a left-handed helix with three residues per turn, and three chains are wound together in a right-handed superhelix to form a rod-like molecule about 1.4 nanometers in diameter and 300 nanometers long. The alpha chains each contain about 1,050 amino acid residues and the molecular weight of the collagen molecule is about 300,000. In each alpha chain within the triple helix every third amino acid residue is glycine. Collagen is characterized by a high content of proline and hydroxyproline amino acids, the absence of tryptophane, a minor amount of aromatic amino acids, and a significant amount of dicarboxylic and dibasic amino acids. At both ends of the collagen molecule there are terminal peptide sequences known as telopeptides which are globular and not triple helical in structure and which lack glycine at every third residue. These telopeptides are the primary sites of internal cross-linking in the molecule and are the most antigenic portions of the collagen molecule.

The collagen molecule which is elaborated by fibroblast cells aggregate in the extracellular matrix of connective tissue to form fibrils which range from 10 to 200 nanometers in diameter. The collagen fibrils aggregate into collagen fibers.

The main sources of collagen for commercial applications are bovine tendons, calf, steer or pig hide. All are readily available at relatively low cost. Generally, reconstituted collagen products are prepared by purification of native collagen by enzyme treatment and chemical extraction. The purified collagen is then dispersed or dissolved in solution, filtered and retained as such, or is reconstituted into fiber, film or sponge by extrusion, casting or lyophilization techniques which are well known to those skilled in the art.

Although the collagen of skin, tendons, bone, cartilage, blood vessels and basement membrane are similar in structure and composition, they do differ slightly in relative amino acid content, amino acid sequence and in architecture. They are products of different genetic loci. The different genetic collagens are known as Type I, II, III, IV, V, etc. The collagen of native skin, tendons, ligaments and bone are primarily Type I collagen with which the present invention is directed.

In preparing the conduits of the present invention, a collagen dispersion is first prepared in a manner well known in the art. One such preparation is taught in U.S. Pat. No. 3,157,524, which is incorporated herein by reference as if set out in full. Another preparation of collagen is also taught in U.S. Pat. No. 3,520,402 which is also incorporated herein as if set out in full.

In particular, the collagen dispersions of the present invention may be prepared by the following methods. It is to be understood, however, that although the preparation of the collagen dispersion is being discussed, there is no criticality in first preparing the collagen dispersion and then adding the purified laminin-containing material thereto. Instead, a laminin-containing dispersion may first be prepared to which is added purified Type I collagen. In either embodiment, the objective will be to ultimately form a dispersion containing Type I collagen and a laminin-containing material.

A native source of Type I collagen, such as, skin, tendons, ligaments or bone is first mechanically or hand cleaned of fat, fascia and other extraneous matter and washed. The cleaned and washed collagen containing material is then comminuted, generally by slicing or grinding.

The material is then subjected to an enzyme treatment while under intermittent stirring with a proteolytic enzyme such as ficin, pepsin, and the like, so as to remove non-collagenous impurities which may cause antigenic activity and to swell the collagen by removing elastin. The amount of enzyme added to the collagen material and the conditions under which enzyme digestion takes place is dependent upon the particular enzyme being used. Generally, when using ficin, which is most commonly used, the pH is adjusted to about 6.0 to 6.3, and the collagen material is digested for about 1 to 2 hours at a temperature of about 36.5° to 37.5° C. with one part ficin for every 150 parts of collagen material. After the requisite amount of time, the enzyme is inactivated by appropriate means well known in the art such as by the addition of a solution of an oxidizing agent such as sodium chlorite as in the case when ficin is used.

The enzyme treated collagen containing material is then washed to remove excess enzyme and the non-collagenous protein impurities. Preferably, the washing is carried out with ultrafiltered and deionized water and optionally further washed with dilute aqueous hydrogen peroxide.

In a preferred embodiment of the present invention, the enzyme digested collagen containing material then may be further subjected to an alkali treatment at a pH of about 13 to 14, at a temperature of about 25° to 30° C. for a period of about 35 to 48 hours, preferably about 40 hours. Suitably, the alkali treatment is carried out in an aqueous solution of 5% sodium hydroxide and 20% sodium sulfate. This optional alkali treatment removes contaminating glycoproteins and lipids. The solution is then neutralized with a suitable acid such as aqueous sulfuric acid and thoroughly washed.

The collagen material, whether subjected to the optional alkali treatment step or not, is then further swollen with a suitable acid solution which acid does not cause any cross linking of the collagen. Such acids are well known to those skilled in the art and include acetic acid, hydrochloric acid, lactic acid, and the like. Regardless of which acid is used, the pH of the acid collagen dispersion is in the range of about 2 to 3.

The dispersed collagen mixture is then homogenized by any conventional means such as a blender or homogenizer so as to further dissociate the fibers and then filtered to remove unswollen, non-collagenous material by means well known in the art such as by passing the dispersion through a 100 mesh stainless steel screen. The resulting filtered collagen dispersion may then be used to prepare the nerve conduits of the present invention.

The other primary constituent that is required to be present in the walls of the conduits of the present invention is a laminin-containing material. As used herein, the phrase "laminin-containing material" is meant to include purified laminin itself or a material which contains laminin and other basement membrane components and is capable of forming a dispersion from which the conduits are made. Materials which contain laminin include basement membranes, human placenta, and an extract of a mouse sarcoma known in the art as Matrigel.

Laminin (a glycoprotein) is an abundant component of all basement membranes. Basement membranes are thin, continuous sheets that separate epithelium from stroma and surround nerves, muscle fibers, smooth muscle cells and fat cells. Basement membranes contain, among other things, Type IV collagen, laminin, nidogen, heparan sulfate proteoglycan and other glycoproteins and proteoglycans.

Human placenta, which contains a large quantity of laminin, is the most desirable source of laminin.

Matrigel is a gel obtained from a mouse sarcoma containing laminin and additional extracellular matrix components. More particularly, it comprises a mixture of about 20% Type IV collagen, about 70% laminin and about 10% heparan sulfate proteoglycan admixed with other minor amounts of extracellular components.

Matrigel and its preparation are described in detail in Kleinman, et al. (1986) *Biochemistry*, 25:312; and in U.S. patent application Ser. No. 771,409, filed Aug. 30, 1985, which is assigned to the United States Government and which is incorporated herein by reference as if set out in full. This gel is available commercially from Collaborative Research Corporation, Lexington, MA.

The Matrigel is prepared from the mouse EHS tumor (maintained at the National Institute of Health, Bethesda, MD) by washing the tumor cells in 3.4M NaCl, 0.05M Tris-HCl, pH 7.4, containing protease inhibitors. The cellular material is then treated with an equal volume (1 ml/gm) of 2M urea, 0.05M Tris-HCl, pH 7.4, overnight at 4° C. and centrifuged at 10,000G for 30 minutes. The residue is washed once with the same volume of buffer, and the extract and wash are combined, dialyzed against 0.15M NaCl in 0.05M Tris-HCl, pH 7.4 (TBS), and centrifuged to remove a small amount of insoluble material. The supernatant contains laminin (approximately 3.5 mg/ml), Type IV collagen (approximately 1.0 mg/ml) and heparan sulfate proteoglycan (approximately 0.1 mg/ml). Nidogen, and other minor components are also present.

Laminin is extracted from materials such as basement membranes and human placenta by means well known to those skilled in the art. Such extraction techniques and a more detailed discussion on laminin is set forth in "Laminin" by Rupert Timple, et al., (*Methods of Enzymology—Structural and Contractile Proteins, Part A. Extracellular Matirx*, Vol. 82, Chap. 47, pp. 831–838, Acadamic Press, 1982) and "Biological Activities of Laminin" by Hynda K. Kleinman, et al., (*Journal of Cellular Biochemistry* Vol. 27, pp. 317–325, 1985), the contents of which are incroporated herein by reference.

In general, the laminin is extracted by a method which is similar to the Matrigel extraction. All procedures are conduced at 4° C. and in the presence of proteases inhibitors to minimize protein degradation. More particularly, human placentas are repeatedly homogenized and washed in 3 to 4M NaCl, preferably 3.4M NaCl, 0.05M Tris, pH 7.4 in the presence of low concentrations of proteases inhibitors, such as 0.004M ethylene diamine tetraacetic acid (EDTA), 0.002M N-ethylmaleimide (NEM), until most of the blood proteins are washed out and the color of the supernatant is no longer pink or red. The residues after washing are collected through centrifugation at 10,000 RPM for 15 minutes. The washed tissue is then extracted in 1.5 to 2.5M urea, preferably in 2M urea (approximately 18% wet tissue per ml of urea) for 16 to 24 hours. After extraction, the material is centrifuged at 10,000 RPM for 15 to 20 minutes and the supernatant is saved. The laminin-containing extract is then dialized in a buffer solution at a pH of 7.4 to eliminate the urea. The buffer is either Tris, HEPES or phosphate buffer, preferably Tris. The laminin is concentrated by passing through a Heparin column (Heparin has a high affinity for laminin and will specifically bind laminin). The laminin is eluted from the column with 0.05M NaCl. The thusly obtained laminin can be further concentrated by precipitating with 30% $NH_4SO_4$ and redissolved in a buffer to any desirable concentration.

The thusly isolated laminin, or alternatively, Matrigel, i.e., the laminin-containing material, may then be combined with the Type I collagen to form a conduit-forming dispersion. The laminin-containing material may be added to the Type I collagen dispersion described above, or in an alternative embodiment, the Type I collagen may be added to a dispersion of the laminin-containing material. Either alternative is applicable in the present invention.

On a dry weight basis, the amount of Type I collagen that is combined in the dispersion with the laminin present in the laminin-containing material is in the ratio of about 90:10 to 40:60. In addition to the Type I collagen and the laminin-containing material, other optional additives may also be present in the dispersion which may aid in the nerve regeneration such as heparin, heparan sulfate proteoglycan, glycosaminoglycans such as hyaluronic acid, chondroitin sulfate and others, growth hormones such as epidermal growth factor (EGF), nerve growth factor, glcoproteins such as fibronectin and the like.

Ultrafiltered and deionized water is added to the dispersion to arrive at a final volume. The final volume is generally dictated by the ultimate wall thickness of the conduit that is desired wherein the greater the volume, the thinner the wall. Typically, for a 1 mm×5 cm conduit having a wall thickness of about 0.06 mm, 15 mg each of collagen and laminin on a dry weight basis may be mixed to a final volume of about 5 to 15 ml, preferably about 8 to 12 ml.

Once the conduit-forming dispersion is formed, a precipitating agent is added to precipitate a fibrous collagen/laminin matrix. Generally, the precipitating agent is an alkali material such as ammonium hydroxide, sodium hydroxide, and the like. The amount of base added to the dispersion is enough to raise the pH to the range of about 4.0 to about 5.5 and preferably from about 4.5 to 5.0. By adding this much base, essentially all of the collagen/laminin will precipitate from the dispersion but will do so at a rate such that there is still ample time to prepare the conduits before interfiber binding has occurred.

After the precipitating agent has been added to the dispersion, it is desireable to then deair the suspension by any suitable means, such as by subjecting it to a vacuum so as to eliminate all of the air bubbles contained within the dispersion.

Before the matrix of collagen and laminin-containing material is fully aggregated, i.e., before interfiber binding takes place, the precipitate is contacted with a spinning mandrel so as to fabricate the conduit.

The precipitated fibrous dispersion may be poured over the mandrel, or alternatively, the mandrel may be inserted into a test tube containing the soft precipitate. The spinning of the mandrel causes the precipitated fibrous matrix of Type I collagen and laminin-containing material to loosely form around and onto the mandrel thereby creating a precursor conduit.

After this precursor conduit is formed, the supernatant is removed (if the embodiment of inserting the mandrel into a test tube is used) and excess liquid is removed from the precursor conduit while it is still on the mandrel. Suitably, while the mandrel is still spinning, the matrix coated mandrel simply may be pressed against the inside of the test tube so as to squeeze out excess liquid. This action not only removes the liquid but also acts to facilitate interfiber binding which is desireable in the final structure.

The matrix of Type I collagen and laminin-containing material, while still on the mandrel in the form of a precursor conduit, is then allowed to dry generally by air drying under a laminar flow hood for about 16 to 24 hours, after which the dried conduits are removed from the mandrel. Preferably, the mandrel is made of or coated with a material which will facilitate the ease of removal of the dried conduit from the mandrel. Suitable coatings include aluminum foil, Teflon, polyethylene, silicone or the like. So too, suitable materials of construction for the mandrel include tungsten, platinum, stainless steel, etc.

The dried conduit is then chemically crosslinked. When collagen is dispersed in an acid solution, many of the natural crosslinks become broken. When the collagen is then reconstituted into a new form, these crosslinks must be replaced in order to restore the unique properties to the fibers. This can be done with chromium sulfate, formaldehye, glutaraldehyde, carbodiimide, adipyl dichloride, and the like, and is commonly known as tanning. The rate at which the conduit of the present invention is resorbed in vivo in a mammal is dependent on the degree of tanning. Factors controlling the extent of crosslinking or tanning are the type and concentration of the tanning agent, the pH and the temperature of incubation. Desireably, the conduits of the present invention are crosslinked to such an extent that they are completely resorbed within 1 to 3 months.

The degree of tanning can be measured by the hydrothermal shrink temperature (Ts) of the conduit, i.e., the temperature at which the conduit in an aqueous envioronment begins to shrink, or by its susceptibility to enzyme digestion, i.e., the more crosslinked the collagen, the longer it will take to digest. The enzyme normally used for enzyme digestion measurement is collagenase.

Generally, the degree of tanning is such that the shrink temperature of the conduits is in the range of from about 45° to about 50° C.

The crosslinked conduits are then thoroughly washed with deionized, ultrafiltered water to remove any excess tanning agent. The conduits are then once again dried by any convenient means such as air drying and are then sterilized by conventional techniques known in the art such as with ethylene oxide or gamma-irradiation.

Generally, the conduits of the present invention have an inner diameter in the range of from about 1 mm to about 1 cm and is dependent upon the size of the nerve gap to be bridged. The wall thickness of the conduits represents a balance between desired permeability and enough compressive strength to prevent collapse. Preferably, the conduits are made as thin as possible while still withstanding suturing and collapse when used in vivo. Suitably, the thickness of the conduits is in the range of from about 0.05 to 0.2 mm and is preferably in the range of about 0.06 mm to 0.1 mm. The length of the conduits vary with the length of the nerve gap that is to be bridged.

While the conduits desireably have a cylindrical cross-section, it is not necessary that they do so. As alternative embodiments of the present invention, the cross-section of the conduits may comprise such shapes as rectangular or any other polygonal shape. Regardless of what shape the cross-section of the conduits takes, the conduits are always hollow and have continuous walls which contain the Type I collagen and laminin-containing material in the form of a matrix. It is contemplated that bundles of such conduits in the form of a honeycomb, for example, may also be employed.

In use, the respective ends of the severed nerve are brought into contact with each end of the conduit, which conduit is longer than the gap to be bridged so that no tension is placed upon the severed nerve. Both the distal and proximal nerve stumps are partially inserted into the conduit and sutured over their perineuerium. Nerve regeneration and resorption of the conduit generally occurs in about 12 weeks time. Using the conduits of the present invention, nerve gaps of up to 15 mm have been bridged.

EXAMPLES

Example I—Preparation of Type I collagen dispersions

Two types of collagen dispersions were prepared for nerve conduit fabrication.

Collagen "B": After the fat and fascia were carefully cleaned from bovine flexor tendons and washed with sodium dodecyl sulfate detergent solution, they were frozen and sliced into approximately 0.1 mm slices with a meat slicer. The tendon slices were then digested in ficin for 1 hour at 37° C. (collagen:enzyme being about 150 w/w). The ficin was subsequently inactivated by adding $NH_4NO_3$ and sodium chlorite. The slices were thoroughly washed with deionized, ultrafiltered water to eliminate excess enzymes and non-collagenous impurities.

Collagen "A": The ficin digested collagen slices were further subjected to an alkali treatment, in the presence of 1.4M NaOH and 1.6M $Na_2SO_4$, at 25°-30° C. for 40 hours. The solution was neutralized with $H_2SO_4$ and the slices were thoroughly rinsed with deionized, ultrafiltered water.

Either Collagen "A" or Collagen "B" was first dispersed in a 0.5% lactic acid solution for about 30 min. The dispersed collagen was then blended in a Waring blender to further dissociate the fibers into a more uniform dispersion. The collagen dispersion was then filtered through a 100 stainless steel mesh screen to define the particle size of the swollen collagen.

Example II—Laminin preparation

While maintaining a temperature of 4° C., human placenta was added to a 2 liter solution containing 397 gms of 3.4M NaCl, 100 ml of 0.05 Tris (pH 7.4), 3.04 gms of 0.004M ethylene diamine tetraacetic acid (EDTA), and 0.5 gms of 0.002M N-ethylmaleimide (NEM) and homogenized in a Waring Blendor. The solution was then centrifuged at 12,000 RPM for 30 minutes. These extraction steps were repeated three times until the supernatant fluid was no longer red or pink.

The tissue was extracted with 1 ml/gm wet weight of tissue overnight with 2.0M urea, 0.05M Tris (7.4 pH), and 0.001M EDTA. The solution was then centrifuged at 10,000 RPM and the supernatant was saved.

An equal volume of 2.0M urea buffer was then added to the residue and the mixture was homogenized. The material was then recentrifuged and the supernatant of this centrifuge step was also saved.

The supernatants were then combined and dialyzed against 0.05M Tris (7.4 pH), 0.001M EDTA, and 0.01M NaCl. The dialyzed material was then passed three times through a column containing heparin sepharose. The column was then rinsed with buffer to remove unbound protein and the bound protein was eluted with 0.5M NaCl. The recovered protein was then dialyzed with 0.05M Tris (pH 7.4) and 0.15M NaCl to form the purified laminin.

Example III—Preparation of Nerve Conduit Using Laminin 15 milligrams of the purified human placenta laminin from Example II were mixed with 5 ml of the collagen dispersion prepared in Example I containing 15 mg of Type I collagen. A final volume of about 12 ml was then obtained by the addition of deionized, ultrafiltered water to the mixture. Approximately 0.5 ml of 0.29% $NH_4OH$ was used to precipitate the collagen/laminin matrix. The collagen/laminin suspension was then deaired under vacuum. The fibrous slurry was then poured into a test tube and a rotating Teflon mandrel was inserted. The matrix of collagen/laminin spun quickly onto the mandrel.

The supernatant was then removed and the mandrel coated with the collagen/laminin matrix pressed against the sides of the test tube so as to remove excess liquid. The matrix while still on the mandrel was then air dried under a laminar flow hood for 20 hours.

The dried conduit was then removed from the mandrel and crosslinked in a 0.3% formaldehyde solution at pH 8 for 15 minutes at ambient temperature. The crosslinked conduits were rinsed several times in pyrogen-free deionized ultrafiltered water and then soaked in additional water for 3 hours to eliminate residual formaldehyde. The conduits were then again air dried under the laminar flow hood.

The conduits were then sterilized with either ethylene oxide or by gamma-irradiation.

Example IV—Preparation of Nerve Conduit Using Matrigel

The procedure of Example III was repeated with the only exception being the use of Matrigel instead of the isolated laminin.

Example V—The Conduit In Use

A total of 28 adult male C57BL/6J mice, approximately two months old at the time of surgery, were used in these studies. All operative procedures were performed under deep anesthesia with Avertin (0.5 gm tribromoethanol dissolved with 2-methyl-2-butanol in 19.5 ml water), i.p., 0.02 ml/g body weight. The left sciatic nerve was exposed and transected at mid-thigh level and allowed to retract for a few minutes before proximal and distal nerve stumps were sutured into a number of different tubular prosthesis approximately 5-6 mm in length, 1 mm inner diameter, and 0.06 mm wall thickness. The final nerve gap distance was approximately 4 mm. After surgery, the animals were housed in a temperature and humidity controlled room with 12 hour light cycles and had access to food and water ad libitum.

Seven different tube compositions were used. The tubes were composed of (1) a hollow tube made of Type I collagen (Collagen "B" of Example I), (2) a hollow tube made of highly purified Type I collagen (Collagen "A" of Example I), (3) a hollow tube made of polyethylene, (4) a polyethylene tube filled in its center with matrigel, (5) a polyethylene tube filled in its center with Vitrogen (a soluble collagen), (6) a conduit of the present invention having a ratio of collagen to matrigel, on a weight basis, of 2:1, and (7) a conduit of the present invention having a ratio of collagen to matrigel, on a weight basis, of 1:5.

In order to quantify the number of primary motor and sensory cells that sent an axon across the nerve gap in terms of rate and extent of in vivo axonal regeneration, the technique set forth in *Brain Research*, 342 (1985) 307–315, by da Silva, et al. was used herein, the contents of said article being incorporated herein as if set out in full.

Briefly, following a survival time of 2 weeks, the animals were processed to display horseradish peroxidase (HRP) labeled cells. More particularly, the distal stump was resectioned 3 mm beyond the original tube and sealed with petrolatum jelly into a new polyethylene tube filled with an HRP solution containing 40% free HRP (Sigma, type VI) and 10% lysolecithin (Sigma) dissolved in a conjugate of WGA-HRP (Vector). Two animals without previous transection or tubular implantation were processed in the same fashion to provide data on the numbers of cells that could be labeled by this technique in control animals. Five additional control animals had their sciatic nerves dissected out and processed exactly as the experimental animals for the quantification of the normal number of myelinated axons.

After an additional 3 days, the animals were perfused transcardially with 100 ml of 0.1M phosphate buffered saline, pH 7.3, followed immediately by 150 ml of 1% paraformaldehyde plus 2% glutaraldehyde, and finally by 100 ml 10% sucrose, each solution made up in the same phosphate buffer. Nerve guides with the enclosed regenerated nerves were then dissected out, post-fixed in 2% osmium tetraoxide, and processed for plastic embedding (DER, Ted Pella, Inc.; Epon 812, Tousimis). One-micron transverse sections were cut from the middle portion of the regenerated nerve cable and stained with alkaline toluidine blue. The number of myelinated axons in these sections was determined with a computer-controlled system. The L3–L5 dorsal root ganglia (DRG) attached to the sciatic nerve and the lumbar enlargement of the spinal cord were removed and embedded in albumin-gelatin. Twenty- or forty-micron longitudinal sections were cut, reacted with tetramethylbenzidine, mounted onto subbed slides, air-dried, stabilized with methylsalicilate and counter-stained with Giemsa. Cells containing HRP were identified and counted at a final magnification of ×400. All filled cells were counted in each section and the numbers obtained were corrected by applying Abercrombie's formula.

The results of this testing are set forth in Table I and II below wherein nerve regeneration characteristics are shown at 2, 4 and 6 weeks (Table I) and at 12 weeks (Table II).

TABLE I

| Tube Composition | Number of Myelinated Axons | | |
|---|---|---|---|
| | 2 wks | 4 wks | 6 wk |
| Collagen A | 5 | 2024 | 3478 |
| Collagen B | 4 | 3451 | 3271 |
| Collagen/Matrigel (1:5) | 41 | 3683 | 2966 |
| Collagen/Matrigel (2:1) | 7 | 3614 | 4039 |

TABLE II

| Tube Composition | Number of Myelinated Axons After 12 Weeks | | |
|---|---|---|---|
| | Backlabeled Spinal Cord Cells (Motor) | Backlabeled Dorsal Root Ganglion Cells (Sensory) | Number of Myelinated Axons |
| Collagen A | 401 +/− 46 | 2016 +/− 94 | 2456 +/− 176 |
| Collagen B | 452 +/− 63 | 1204 +/− 332 | 2845 +/− 262 |
| Polyethylene | 587 +/− 70 | 1707 +/− 139 | 1681 +/− 218 |
| Polyethylene/Matrigel | 882 +/− 29 | 1758 +/− 167 | 2332 +/− 91 |
| Polyethylene/Vitrogen | 650 +/− 107 | 1589 +/− 321 | 2176 +/− 245 |
| Collagen/Matrigel (2:1) | 603 +/− 27 | 2177 +/− 105 | 2988 +/− 100 |
| Collagen/Matrigel (1:5) | 537 +/− 43 | 1677 +/− 280 | 2853 +/− 302 |
| Normal | 848 +/− 21 | 4169 +/− 30 | 3850 +/− 24 |

As is readily seen from the Tables, particularly Table II, the conduits of the present invention had a substantially greater number of myelinated axons than any of the other tube devices. Moreover, it is also noted from Table I that the conduits of the present invention also substantially increase the initial rate at which the axons grow across the transection site.

What is claimed is:

1. A hollow conduit for promoting the in vivo regeneration of a severed mammalian nerve so as to bridge a gap between its severed ends having walls comprised of a matrix of Type I collagen and laminin-containing material.

2. The hollow conduit of claim 1, wherein the Type I collagen is derived from bovine tendons.

3. The hollow conduit of claim 1, wherein the laminin-containing material is purified human placenta laminin.

4. The hollow conduit of claim 1, wherein the laminin-containing material is derived from basement membrane.

5. The hollow conduit of claim 1 having an inner diameter of about 1 mm to 1 cm.

6. The hollow conduit of claim 1 having a wall thickness of about 0.05 to 0.2 mm.

7. The hollow conduit of claim 1 wherein the amount of Type I collagen present to the amount of laminin-containing material is in the ratio of about 90:10 to 40:60.

8. The hollow conduit of claim 1 wherein the walls further contain any of the group consisting of glycoproteins, proteoglycans, heparan sulfate proteoglycan, nidogen, glycosaminoglycans, fibronectin, epidermal growth factor or nerve growth factors, or combinations thereof.

9. A method of promoting in vivo regeneration of a mammalian severed nerve so as to bridge a gap between its severed ends comprising bringing the respective ends of the severed nerve into contact with each end of a hollow conduit whose walls are comprised of a matrix of Type I collagen and laminin-containing material.

10. The method of claim 9, wherein the ends of the severed nerve are sutured to each respective end of the conduit.

* * * * *